United States Patent [19]

Thominet

[11] 3,954,748

[45] May 4, 1976

[54] 3-ALKOXY-THIANAPTHENE-2-CARBOXAMIDES

[75] Inventor: Michel Leon Thominet, Paris, France

[73] Assignee: Societe d'Etudes Scientifiques et Industrielles de l'Ile-de-France, Paris, France

[22] Filed: June 26, 1974

[21] Appl. No.: 483,246

Related U.S. Application Data

[63] Continuation-in-part of Ser. No. 348,297, April 5, 1973, Pat. No. 3,838,169, which is a continuation-in-part of Ser. No. 140,605, May 5, 1971, Pat. No. 3,745,175, which is a continuation-in-part of Ser. No. 845,509, July 28, 1969, abandoned.

[30] Foreign Application Priority Data

July 29, 1968   France .............................. 68.161060
Oct. 28, 1968   France .............................. 68.171684

[52] U.S. Cl. ...................... 260/247 P; 260/268 BC; 260/293.57; 260/309.7; 260/326.35; 260/330.5; 424/248; 424/250; 424/267; 424/274; 424/275

[51] Int. Cl.$^2$...................................... C07D 333/70
[58] Field of Search ................. 260/330.5, 247.1 P, 260/268 BC, 293.57, 309.7, 326.35

[56]  References Cited
UNITED STATES PATENTS

| | | | |
|---|---|---|---|
| 2,876,235 | 3/1959 | Voegtli ............................ | 260/330.5 |
| 3,622,574 | 11/1971 | Wright et al. ................ | 260/247.1 P |
| 3,651,094 | 2/1972 | Libis et al. ....................... | 260/330.5 |

OTHER PUBLICATIONS

Campaigne et al.; Chem. Abst. 68: 68811z, (1968).

*Primary Examiner*—Lorraine A. Weinberger
*Assistant Examiner*—Michael Shippen
*Attorney, Agent, or Firm*—Frank M. Nolan

[57]    ABSTRACT

The 3-alkoxy-thianaphthene-2-carboxamides of this invention are effective for the treatment of mammals afflicted with emesis. When administered to dogs in dosages of 250 µg/kg, compounds of this invention give 100% protection against vomiting normally induced by subcutaneous administration of apomorphine. The compounds of this invention also favorably modify behavior disturbances in mammals.

2 Claims, No Drawings

3-ALKOXY-THIANAPTHENE-2-CARBOXAMIDES

This application is a continuation-in-part of the application Ser. No. 348,297, filed Apr. 5, 1973 now U.S. Pat. No. 3,838,169. The application Ser. No. 348,297 is a continuation-in-part of the U.S. Pat. application Ser. No. 140,605, filed May 5, 1971, now U.S. Pat. No. 3,745,175. U.S. patent application Ser. No. 140,605 is in turn a continuation-in-part of the application Ser. No. 845,509, filed July 28, 1969, now abandoned.

This invention relates to 3-alkoxy-thianaphthene-2-carboxamides and more particularly to such carboxamides, the dioxides thereof and the pharmaceutically acceptable acid addition salts and quaternary ammonium salts of such carboxamides.

The invention also includes methods of treatment of behavior disturbances or emesis of mammals with such compounds.

The 3-alkoxy-thianaphthene-2-carboxamides of this invention have the formula:

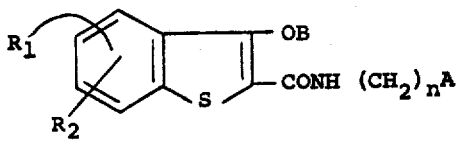

(1)

in which $R_1$ and $R_2$ are the same or different and are hydrogen, lower alkoxy, preferably having less than 5 carbon atoms, halogen (such as fluorine, chlorine, bromine or iodine), nitro or amino. Examples of lower alkoxy are methoxy, ethoxy and isopropoxy. B is allyl or lower alkyl, preferably having less than 5 carbon atoms, such as methyl, ethyl and n-propyl; and $n$ is 1, 2 or 3. A is mono lower alkylamino, di lower alkylamino, a 5 or 6 membered heterocyclic nitrogenous monovalent radical with or without oxygen, nitrogen-lower alkyl, nitrogen-allyl or an additional nitrogen atom connected through a nitrogen atom of the heterocyclic radical to the terminal methylene group of formula (1) or a monovalent radical having the formula:

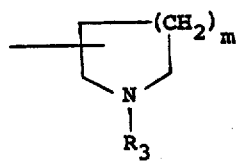

(2)

in which $m$ is 1 or 2 and $R_3$ is allyl or lower alkyl, preferably having less than 5 carbon atoms. Preferably, all of the lower alkylamino radicals and the lower alkyl groups of the 5 or 6 membered heterocyclic nitrogenous monovalent radical have less than 7 carbon atoms, such as methyl, ethyl, propyl, isobutyl and amyl. Examples when A is a heterocyclic nitrogenous monovalent radical are piperidinyl, pyrrolidinyl, imidazolidinyl, piperazino and morpholino.

This invention also includes the 1,1-dioxides, and the pharmaceutically acceptable acid addition salts and the quaternary ammonium salts of the 3-alkoxy-thianaphthene-2-carboxamides of formula (1). The acid addition salts may be of organic acids, such as acetic acid, succinic acid or citric acid or inorganic acids, such as hydrochloric acid, sulfuric acid or phosphoric acid. If the 3-alkoxy-thianaphthene-2-carboxamides or their derivatives of this invention have one or more asymmetric carbon atoms, they may exist as the dextro or levo forms or racemic mixtures.

The preparation of the compositions of this invention comprises cycling a substituted or unsubstituted alkyl 2-carbomethoxymethylthio benzoate with the aid of an alkali metal alcoholate, as sodium methylate, to obtain a substituted or unsubstituted alkyl 3-hydroxythianaphthene-2-carboxylate which is alkylized by means of an alkylizing agent such as dimethyl sulfate or ethyl p-toluene sulfonate. The substituted or unsubstituted 3-methoxythianaphthene-2-carboxylic acid obtained by saponification of the ester is then converted to an amide by the desired amine.

The quaternary ammonium salts of the 3-alkoxy-thianaphthene-2-carboxamides are prepared by reacting a 3-alkoxy-thianaphthene-2-carboxamide free base with an alkyl halide such as methylbromide. Desirably, each of the reactants is dissolved in an inert solvent such as acetone. The product may be purified by conventional filtration, evaporation and recrystallization procecures.

A more comprehensive understanding of this invention is obtained by reference to the following examples:

EXAMPLE 1

N-(DIETHYLAMINOETHYL)-3-METHOXY-THIANAPHTHENE-2-CARBOXAMIDE

Stage A. 2-carboxy-methylthio-benzoic acid

Into a 1 liter flask equipped with an agitator, a thermometer and a dropping funnel, there is introduced 137 g (1 mole) of anthranilic acid, 200 ml of water and 105 ml of concentrated hydrochloric acid. The mixture is heated to complete dissolution, and then 105 ml of concentrated hydrochloric acid is added. The hydrochloride of the anthranilic acid precipitates in the form of a very thick mass. It is cooled to about 0°C and into the pasty mixture there is poured drop by drop a solution of 69 g (1 mole) of sodium nitrite in 140 ml of water. The temperature is maintained between 0° and 5°C.

A brown solution is obtained which is agitated for 1 hour between 0° and 5°C. The excess hydrochloric acid is neutralized by the addition of 150 g of potassium acetate, to obtain a pH of about 4.

The diazoic solution thus obtained is poured dropwise into a solution containing 320 g of potassium xanthate (2 mole) in 440 ml of water. The operation is done at between 75° and 80°C. The nitrogen separates rapidly and the solution becomes cloudy. After cooling, the product is precipitated by the addition of 160 ml of hydrochloric acid. The precipitated product is drained and washed on a filter with water. The product is then put in suspension in 400 ml of water, and 200 ml of sodium hydroxide and the mixture is heated for 2 hours in a bainmarie. The solid dissolves, giving a brown-red solution. To this solution there is added dropwise a solution of 132 g (0.9 mole + excess of 50%) of chloracetic acid dissolved in 100 ml of water to which is added 140 ml of 30% sodium hydroxide.

The solution thus obtained is heated for 2 hours at reflux, the pH being maintained at about 3. It is then cooled and 16 ml of sodium hydroxide is added to take the pH to 7.8.

The solution is filtered, passed through charcoal and the acid is precipitated with 150 ml of hydrochloric acid. There are obtained 153 g (yield: 72%) of 2-carboxy-methylthiobenzoic acid (m.p.: 214°–215°C).

Stage B. Methyl-2-carbomethoxymethyl-thio-benzoate

Into a 2 liter flask equipped with a reflux refrigerant, there are introduced 450 g of methyl alcohol, then in small portions, while cooling, 232 g of 100% sulfuric acid and then 128 g of 2-carbomethylthio-benzoic acid (0.6 mole). There is obtained a red suspension which dissolves under heat. The mixture is refluxed for 9 hours. There is then distilled one part of alcohol and the remaining solution is poured into 4 liters of water containing 254 g of sodium carbonate. The methyl 2-carbomethoxy-methyl-thio-benzoate precipitates. It is drained, washed with water until the sulfate ions are eliminated, and air-dried. There are obtained 113 g of product, (m.p.: 49°–50°C) (yield: 65%).

Stage C. Methyl 3-hydroxy-thianaphthene-2-carboxylate

In a 500 ml flask equipped with a reflux refrigerant there is dissolved 9 g of sodium in 180 ml of methyl alcohol. The mixture is cooled and there is added in small portions 95 g (0.40 mole) of methyl 2-carbomethoxy-methyl-thio-benzoate. There is observed no dissolution, but there is immediate transformation of the ester in sodium salt of thianaphthene formed in the form of a thick yellow precipitate. When the introduction is terminated, the mixture is allowed to react for 4 hours at room temperature. The precipitate is redissolved by the addition of 1.8 liter of water. The solution is filtered and passed through charcoal. The methyl 3-hydroxy-thianaphthene-2-carboxylate is then precipitated by the addition of 50 ml of acetic acid. It is drained, washed with water and dried. There are obtained 73 g of product. (yield: 89%) (m.p.: 105°–106°C).

Stage D. Methyl-3-methoxy-thianaphthene-2-carboxylate

In a flask equipped with an impervious agitator, a reflux refrigerant and a thermometer, there is dissolved 50 g (0.24 mole) of methyl 3-hydroxy-thianaphthene-2-carboxylate in 250 ml of acetone at about 40°C. There is added 33 g of methyl sulfate, then 33 g of potassium carbonate. There is obtained a suspension which is refluxed for 3 hours. One part of the acetone is distilled and the residue reclaimed by the addition of 500 ml of water. The methyl 3-methoxy-thianaphthene-2-carboxylate precipitates. It is drained, washed with water and dried. 52 G of product is obtained. (yield: 99%) (m.p.: 66°–67°C).

Stage E. 3-methoxy-thianaphthene-2-carboxylic acid

In a 250 ml flask equipped with a reflux refrigerant, there is dissolved 52 g (0.23 mole) of methyl 3-methoxy-thianaphthene-2-carboxylate in 75 ml of 95% alcohol. There is added 24 ml of sodium hydroxide and the mixture is brought to reflux in a water bath. The sodium salt of thianaphthene-carboxylic acid formed precipitates and forms a mass at the start of heating. The reflux is maintained for two hours and the precipitate recovered in 750 ml of water. The solution obtained is filtered and passed through charcoal, and then the 3-methoxy-thianaphthene-2-carboxylic acid is precipitated by 25 ml of hydrochloric acid. The product is drained, washed in water until the chlorine ions are eliminated and dried at about 50°C. There are obtained 46 g of product. (yield: 96%) (m.p.: 182°–183°C).

Stage F. 3-Methoxy-thianaphthene-2-carbonyl chloride

Into a 250 ml flask equipped with a reflux refrigerant, there are introduced 50 g of thionyl chloride and 44 g (0.21 mole) of 3-methoxy-thianaphthene-2-carboxylic acid. The mixture is heated in a water-bath at 50°C. until it is completely dissolved. The excess thionyl chloride is then distilled under vacuum. The solid residue is reclaimed with 50 ml of petroleum ether. The 3-methoxy-thianaphthene-2-carbonyl chloride is drained, washed with petroleum ether and dried under vacuum. There are obtained 47 g of product. (yield: 99%) (m.p.: 93°–94°C).

Stage G. N-(diethylaminoethyl)-3-methoxy-thianaphthene-2-carboxamide

In a 500 ml flask with thermometer, agitator and dropping funnel, there are introduced 24 g (0.205 mole) of diethylaminoethylamine and 150 ml of methylethylketone. It is cooled at 5°C and there is then added in small portions 3-methoxy-thianaphthene-2-carbonyl chloride. At the end of 2 hours the thianaphthene-carboxamide hydrochloride formed partially crystalizes. It is recovered in 500 ml of water.

The solution obtained is filtered and the base is precipitated by the addition of 30 ml of ammonia. It is decanted, and the aqueous solution is extracted with ether. The organic solution obtained is washed in water and dried on potassium carbonate. The ether is then completely distilled under vacuum. There are obtained 46 g of N-(diethylaminoethyl)-3-methoxy-thianaphthene-2-carboxamide (yield; 84%) in the form of an orange-red liquid.

Stage H.

The base obtained in the preceding stage is dissolved in 40 ml of absolute alcohol, and 16 g of 85% of phosphoric acid dissolved in 40 ml of absolute alcohol is added. The phosphate of N-(diethylaminoethyl)-3-methoxy-thianaphthene-2-carboxamide precipitates. It is drained, washed with 50 ml of absolute alcohol and dried at 60°C. It is a white solid. (m.p.: 173°–174°C).

EXAMPLE II

N-(1-ETHYL-2-PYRROLIDYLMETHYL)-3-METHOXY-THIANAPHTHENE-2-CARBOXAMIDE

Stage A through F are the same as those described in Example I.

Stage G.

Into a 500 ml flask equipped with an agitator and a thermometer, there are introduced 26 g (0.205 mole) of 1-ethyl-2-aminomethylpyrrolidine and 150 ml of methylethylketone, and while maintaining the temperature between 5° 5 and 10° C there are added in small portions, 47 g (0.207 mole) of 3-methoxy-thianaphthene-2-carbonyl chloride.

After the introduction is terminated, agitation is continued while allowing the temperature to mount. The solution obtained is then recovered with 500 ml of water. All the solvent is removed and the base is precipitated by the addition of 30 ml of ammonia. This base is extracted with ether and the ether dried after washing in water on potassium carbonate.

The solvent is then completely distilled under vacuum. There are obtained 58 g of N-(1-ethyl-2-pyrrolidylmethyl)-3-methoxy-thianaphthene-2-carboxamide in the form of a violet liquid. (yield: 89%)

Stage H. Phosphate of N-(1-ethyl-2-pyrrolidylmethyl)-3-methoxy-thianaphthene-2-carboxamide There are dissolved 55 g (0.17 mole) of 1-ethyl-2-pyrrolidylmethyl-3-methoxy-thianaphthene-2-carboxamide in 100 ml of 95% alcohol and to that solution is added 20 g of 85% phosphoric acid dissolved in 100 ml of alcohol at 95°C. The phosphate of N-(1-ethyl-2-pyrrolidylmethyl)-3-methoxy-thianaphthene-2-carboxamide formed crystalizes. It is drained and washed with 50 ml of 95% alcohol and dried at room temperature. It is a white solid. (m.p.: 177°–178°C).

EXAMPLE III

N-(DIETHYLAMINOETHYL)-1,1-DIOXY-3-METHOXY-THIANAPHTHENE-2-CARBOXAMIDE

Stage A. 2-(carboxymethyl-sulfonyl)-benzoic acid

Into a 3 liter flask equipped with a reflux and agitator, there are introduced 178 g (0.84 mole) of 2-carboxymethylthiobenzoic acid and 50 ml of acetic acid. There is obtained a suspension to which 550 ml of hydrogen peroxide solution to 102 volumes is added in small portions. The mixture is heated at 70° for 6 hours. The solution obtained becomes yellow, then greenish. It is heated for 4 hours at reflux until the oxygen is completely released. After the acetic acid and the water have been removed under vacuum, the 2-(carboxy-methylsulfonyl)-benzoic acid formed crystalizes. It is drained, placed in suspension in 150 ml of benzene, again refiltered and washed on the filter with benzene. There are obtained 191 g of product. (yield: 93%) (m.p.: 161°–162°C).

Stage B. Methyl 2-(carbomethoxymethylsulfonyl)-benzoate

Into a 2 liter flask equipped with a reflux and agitator, there are introduced 585 g of methyl alcohol, then there is poured in small portions 310 g of 100% sulfuric acid and 191 g (0.78 mole) of 2-carboxymethylsulfonyl-benzoic acid are added. The mixture is refluxed for 9 hours. After one part of the alcohol has been removed under vacuum, the residue is poured into 5 liters of water containing 335 g of sodium carbonate. The ester formed precipitates. It is drained, washed in water until the sulphate ions are eliminated and dried at 40°C. There are obtained 169 g of methyl 2-(carbomethoxymethylsulfonyl)-benzoate. (yield: 80%) (m.p.: 102°–103°C).

Stage C. Methyl 1,1-dioxy-3-hydroxythianaphthene-2-carboxylate

In a 1 liter flask equipped with an agitator and a reflux and refrigerant there are dissolved 14 g of sodium (0.62 mole) in 500 ml of methyl alcohol. To the solution of sodium methylate obtained, there are added 169 g (0.62 mole) of methyl 2-carbomethoxymethylsulfonyl benzoate. The product dissolves progressively. Agitation is continued constantly for 4½ hours at room temperature. Then 5 liters of water are added. The methyl 1,1-dioxy-3-hydroxy-thianaphthene-2-carboxylate is then precipitated by the addition of hydrochloric acid. It is drained, washed with water until the chloride ions are eliminated and dried at ordinary temperature. There are obtained 126 g (yield: 84.5%) of product melting at 189°–190°C.

Stage D. Methyl 1,1-dioxy-3-chloro-thianaphthene-2-carboxylate

Into a 500 ml flask equipped with a reflux refrigerant, there are introduced 132 g (0.55 mole) of 1,1-dioxy-3-hydroxy-thianaphthene-2-methyl carboxylate, then 264 g of thionyl chloride and 5.5 ml of pyridine. A slurry is obtained when heated at reflux on a bain-marie. Heating is continued for 4 hours. Then the excess of thionyl chloride is removed. There remains 216 g of a crystalized, yellow product which is recovered with 400 ml of petroleum ether, drained and washed with 350 ml of petroleum ether and dried quickly. This product formed of methyl 1,1-dioxy-3-chloro-thianaphthene-2-carboxylate is put immediately into reaction by the following step.

Stage E. Methyl 1,1-dioxy-3-methoxy-thianaphthene-2-carboxylate

In a 1 liter flask equipped with an impervious agitator, a reflux refrigerant and a thermometer, there are dissolved 32 g (2.5 × 0.35 mole) of sodium in 400 ml of methyl alcohol. The product of Stage D is then added, avoiding a temperature rising up to 20°C. There is obtained an orange solid. After 4 hours, 4 liters of water are added. The precipitated product is drained, washed with water and dried. There are obtained 30 g (yield: 21%) of methyl 1,1-dioxy-3-methoxy-thianaphthene-2-carboxylate (m.p.: 162°–163°C).

Stage F. N-(diethylaminoethyl)-1,1-dioxy-3-methoxy-thianaphthene-2-carboxamide

Into a 500 ml flask equipped with an agitator, a thermometer and a dropping funnel, there are introduced 33 g (0.13 mole) of methyl 1,1-dioxy-3-methoxy-thianaphthene-2-carboxylate and 165 ml of ethylene glycol.

This is heated at 110°C to obtain a dissolution of the product and the temperature is allowed to return to 30°C. At that time there are added dropwise through the dropping funnel 18 g (0.15 mole) of diethylamino-ethyl-amine. The reaction is violent. The temperature rises rapidly to 45°–50°C. When the introduction is finished, agitation is continued for an hour at about 25°C. Then 600 ml of water are added and the product obtained is drained. This product is recrystallized in 100 ml of absolute alcohol. There are obtained 39 g (yield: 81%) of N-(diethylaminoethyl)-1,1-dioxy-3-methoxy-thianaphthene-2-carboxamide (m.p.: 135°–136°C).

Stage G. Hydrochloride of N-(diethylaminoethyl)-1,1-dioxy-3-methoxy-thianaphthene-2-carboxamide The product obtained in the preceeding Stage F is dissolved in 150 ml of absolute alcohol and there is added an alcoholic solution of 3.4 g of gaseous hydrochloric acid in 1 liter of alcohol. The hydrochloride of N-(diethylaminoethyl)-1,1-dioxy-3-methoxy-thianaphthene-2-carboxamide formed precipitates. It is drained, washed in alcohol and air-dried. It is a white solid. (m.p.: 203°C) (yield: 94%).

EXAMPLE IV

N-(1-ETHYL-2-PYRROLIDYLMETHYL)-3-METHOXY-THIANAPHTHENE-1,1-DIOXY-2-CARBOXAMIDE

Stages A through E are the same as those described in Example III.

Stage F.

Into a 1 liter flask equipped with an agitator, a thermometer and a dropping funnel, there are introduced 57 g (0.224 mole) of methyl 3-methoxy-thianaphthene-1,1-dioxy-2-carboxylate and 285 ml of ethylene glycol. The mixture is heated to 40°C and at that temperature there are added dropwise 29 g (0.225 mole) of 1-ethyl-2-aminomethyl-pyrrolidine. After the introduction is terminated, agitation is continued for 3 hours. The mixture is cooled and 1 liter of water is added. The solid product obtained is drained, washed with water and dried. After recrystallization of this product in alcohol, there are obtained 61 g (yield: 78%) of N-(1-ethyl-2-pyrrolidylmethyl)-3-methoxy-thianaphthene-1,1-dioxy-2-carboxamide. (m.p.: 112-113°C).

Stage G. Hydrochloride of N-(1-ethyl-2-pyrrolidylmethyl)-3-methoxy-thianaphthene-1,1-dioxy-2-carboxamide 44 G of N-(1-ethyl-2-pyrrolidylmethyl)-3-methoxy-thianaphthene-1,1-dioxy-2-carboxamide are dissolved in 100 ml of absolute alcohol. To this solution are added 4.6 g of gaseous hydrochloric acid dissolved in 30 ml of alcohol. The hydrochloride of N-(1-ethyl-2-pyrrolidylmethyl)-3-methoxy-thianaphthene-1,1-dioxy-2-carboxamide formed is drained, washed on a filter with absolute alcohol and dried. There are obtained 47 g of a white solid. (yield: 96.5%) (m.p.: 212°-213°C).

EXAMPLE V

N-(DIETHYLAMINOETHYL)-3,5,6-TRIMETHOXY-THIANAPHTHENE-2-CARBOXAMIDE

Stage A. Methyl 3,4-dimethoxy-6-nitro-benzoate

In a 2 liter flask equipped with an agitator, there are introduced 560 ml of 40% nitric acid, then 144 g (0.74 mole) of methyl 3,4-dimethoxy benzoate. Agitation is maintained at room temperature. Little by little, the liquid becomes thicker and at the end of four hours there is obtained a thick paste. It is allowed to stand overnight. The nitric derivative is diluted with a little water, drained and washed with water until neutralized. There are obtained 144 g (yield: 81%) of methyl 3,4-dimethoxy-6-nitro-benzoate. (m.p.: 143°-144°C).

Stage B. Methyl 3,4-dimethoxy-6-aminobenzoate

In an hydrogenating autoclave, there are placed 144 g of methyl 3,4-dimethoxy-6-nitro-benzoate, 300 ml of tetrahydrofuran and 3 coffee spoonfuls of Raney nickel. Hydrogenation occurs at about 35°C. In 20 minutes, the pressure drop is 80 kg. It is cooled, the nickel filtered, and the tetrahydrofuran removed under vacuum. There are obtained 123 g (97%) of methyl 3,4-dimethoxy-6-aminobenzoate. (m.p.: 130°C).

Stage C. 2-Carboxymethyl-thio-4,5-dimethoxy benzoic acid

Into a 2 liter flask equipped with an agitator, a thermometer and a dropping funnel, there are introduced 113 g (0.54 mole of methyl 3,4-dimethoxy-6-aminobenzoate, 215 ml of water and 107 ml of concentrated hydrochloric acid. A thick suspension is obtained which is heated to complete dissolution, then cooled to 0°C so that the hydrochloride formed crystalizes. Then there is introduced dropwise a solution of 37 g of sodium nitrite in 275 ml of water, the temperature being maintained between 0° and 5° C. The precipitate dissolves progressively. There is obtained a clear solution which is neutralized by the addition of 18 g of potassium carbonate, so as to raise the pH to 4.

In a 2 liter flask equipped with an agitator, a thermometer and a dropping funnel, there are dissolved 128 g of potassium xanthate in 220 ml of water. The solution is heated at 75° C and then pours slowly, dropwise, the diazoic solution obtained previously. The xanthogenic ester formed separates in the form of an oily bed. It is allowed to cool. The organic product is extracted in ether. The etherized solution is washed in soda, then in water and dried on sodium sulfate. 160 g of the xanthogenic derivative is obtained (yield: 94%).

To the xanthogenic derivative is added a hydroalcoholic solution of potash obtained by dissolving 130 g of potassium hydroxide in a mixture of 415 ml of alcohol and 70 ml of water. It is heated at reflux and cooled. The solution is diluted with 3 liters of water and the acid precipitated with 180 ml of concentrated hydrochloric acid.

After cooling, it is drained and washed with water until the chlorine ions disappear. The raw and moist product thus obtained is immediately put in reaction with the sodium chloroacetate. By adding to this product 48g of chloracetic acid dissolved in 36 ml of water and 50 ml of soda and heating the mixture obtained at reflux for 3 hours, there is obtained a cloudy solution which is diluted with 2 liters of water and filtered after passage through charcoal. The 2-carboxy-methylthio-4,5-dimethoxy benzoic acid formed is then precipitated by the addition of 70 ml of concentrated hydrochloric acid. It is drained, washed in water until the chlorine ions are eliminated and dried at ordinary temperature. There are obtained 111g of product (yield: 77%) (m.p.: 227°-228° C).

Stage D. Methyl 2-(carbomethoxymethylthio)-4,5-dimethoxy-benzoate

Into a 1 liter flask equipped with a reflux refrigerant, are put 300 g of methyl alcohol and 164 g of 100% sulfuric acid are poured in, in small portions. Then 110 g of 2-carboxymethylthio-4,5-dimethoxy-benzoic acid are added. The organic acid dissolves little by little and after heating for 3 hours, the ester begins to crystalize. The reflux is continued for 9 hours. The reaction mixture is then poured into 3 liters of water containing 195 g of sodium carbonate. The methyl 2-carbomethoxymethylthio-4,5-dimethoxy-benzoate formed is drained, washed in water until the sulfate ions are eliminated, and air-dried. There are obtained 105 g of product (yield: 86%) (m.p.: 120°-121° C).

Stage E. Methyl-3-hydroxy-5,6-dimethoxy-thianaphthene:2-carboxylate

In a 1 liter flask equipped with an impervious agitator, a reflux refrigerant and a thermometer, there are dissolved 8 g of sodium in 315 ml of alcohol. Then 105 g (0.35 mole) of methyl 2-carbomethoxymethylthio-4,5-dimethoxy-benzoate are introduced in small portions. The ester begins to dissolve and then the sodium salt precipitates rapidly.

When the introduction is ended, the mixture is heated at reflux for 3 hours. The precipitate is then redissolved in 3 liters of water. There remains an insoluble gelatinous substance which is filtered. The methyl 3-hydroxy-5,6-dimethoxy thianaphthene-2-carboxylate formed is precipitated by the addition of 70 ml of acetic acid. The precipitate is drained, washed in water and dried at 60° C. There are obtained 82 g of product (yield: 88%) (m.p.: 184°-185° C).

Stage F. Methyl 3,5,6-trimethoxy-thianaphthene-2-carboxylate

In a 2 liter flask equipped with an impervious agitator, a reflux refrigerant and a thermometer, there are introduced 82 g (0.305 mole) of methyl 3-hydroxy-5,6-dimethoxy-thianaphthene-2-carboxylate, 575 ml of acetone and 42 g of potassium carbonate. There are added 42 g of methyl sulfate in small portions. The mixture is heated at reflux for 5 hours. Then the acetone is distilled and the residue recovered with 2 liters of water. The methyl 3,5,6-trimethoxy-thianaphthene- 2-carboxylate formed precipates. It is drained, washed with water and air-dried. There are obtained 83 g of product melting at 132°–133° C (yield: 95%).

Stage G. N-(diethylaminoethyl)-3,5,6-trimethoxy-thianaphthene-2-carboxamide

In a 250 ml flask with a Vigreux column of 40 cm, there are introduced 32 g (0.113 mol) of methyl 3,5,6-trimethoxy-thianaphthene-2-carboxylate, 90 ml of xylene, 20 g of diethylaminoethylamine and 5.7 g of aluminum isopropylate. There is obtained a suspension which is heated gently so as to distill the alcohol formed in the form of its azeotrope with the xylene. The duration of the reaction is 1½ hours in total. After cooling, the solution is recovered with 400 ml of water and 30 ml of concentrated hydrochloric acid.

The N-(diethylaminoethyl)-3,5,6-trimethoxy-thianaphthene-2-carboxamide formed passes in the aqueous solution in the form of hydrochloride. The aqueous solution is filtered and the amine is precipated with 35 ml of soda until turning red to phenolphthalein.

After cooling, it is drained, washed with water until the chlorine ions are eliminated and dried at 40° C. There are obtained 23 g (yield: 56%) of N-(diethylaminoethyl)-3,5,6-trimethoxy-thianaphthene-2-carboxamide (m.p.: 128–129°C).

EXAMPLE VI

N-(1-ETHYL-2-PYRROLIDYLMETHYL)-3,5,6-TRIMETHOXY-THIANAPHTHENE-2-CARBOXAMIDE

Stages A through F are the same as those described in Example V.

Stage G. N-(1-ethyl-2-pyrrolidylmethyl)-3,5,6-trimethoxy-thianaphthene-2-carboxamide In a 1 liter flask with a 40 cm Vigreux column, there are introduced 85 g (0.3 mole) of methyl 3,5,6-trimethoxy-thianaphthene-2-carboxylate, 250 ml of xylene, 46 g of 1-ethyl-2-aminomethyl-pyrrolidine and 15.5 g of aluminum isopropylate and the flask is gently heated so as to distill the alcohol in the form of its azeotrope with xylene. The reaction lasts about 1 hour. The solution obtained is recovered, after cooling, with 600 ml of water and 85 ml of concentrated hydrochloric acid. The aqueous solution is decanted and the xylene layer is washed twice with hydrochloric water.

The aqueous solutions are joined, filtered with charcoal and the base is precipitated with 120 ml of soda lye. It is a liquid which is decanted. The aqueous solution is extracted in methylene chloride and the organic solution dried on potassium carbonate.

The solvent is then distilled under vacuum to a constant weight. The residue is recrystalized in 60 ml of isopropyl alcohol. There are obtained 29 g (yield: 30%) of N-(1-ethyl-2-pyrrolidylmethyl)-3,5,6-trimethoxy-thianaphthene-2-carboxamide (m.p.: 113°–114° C).

EXAMPLE VII

N-(DIETHYLAMINOETHYL)-3-METHOXY-5-AMINO-THIANAPHTHENE-2-CARBOXAMIDE

Stage A. 2-carboxymethylthio-5-nitrobenzoic acid

In a 5 liter flask equipped with an impervious agitator, a reflux refrigerant and a thermometer, there are introduced 146 g (0.72 mole) of 2-chloro-5-nitro-benzoic acid and 2200 ml of cellosolve. There is obtained a solution to which is added 181 g of sodium bicarbonate and 66 g of thio-glycolic acid. The mixture is refluxed. There is very rapid precipitation of the sodium salt of the carboxymethylthio acid formed. After 3½ hours of reflux, the heating is stopped, and the sodium salt is cooled, drained and washed on a filter with 200 ml of cellosolve. This salt is then redissolved in water and the acid is precipitated with 145 ml of concentrated hydrochloric acid. It is drained, washed with water until the chloride ions are eliminated and dried at 50° C. There are obtained 159 g (yield: 86%) of 2-carboxymethylthio-5-nitro-benzoic acid (m.p.: 216°–217° C).

Stage B. Methyl 2 (carbomethoxymethylthio)-5-nitrobenzoate

In a 2 liter flask equipped with a reflux and refrigerant, there are introduced 465 g of methyl alcohol and 250 g of sulfuric acid poured in small portions. There are added 159 (0.62 mole) of 2-carbomethoxymethylthio-5-nitro-benzoic acid. The mixture is refluxed for 9 hours. It is cooled and the reaction mixture is poured into 6 liters of water containing 270 g of sodium carbonate.

The methyl 2-(carbomethoxymethylthio)-5-nitro-benzoate formed is drained, washed with water until the sulfate ions are eliminated and dried at 40° C. There are obtained 170 g of product (yield: 96% (m.p.: 116°–120° C)

Stage C. Methyl 3-hydroxy-5-nitro-thianaphthene-2-carboxylate

In a two-tube, 3 liter flask, there are dissolved 13.7 g of sodium in 510 ml of methyl alcohol; then there are mounted on the flask an impervious agitator, a reflux, refrigerant and a thermometer. There are introduced 170 g (0.6 mole) of methyl 2-carbomethoxymethylthio-5-nitro-benzoate in small portions.

Agitation is continued for 5 hours. Then the thianaphthene formed is precipitated by the addition of 5 liters of water and 300 ml of acetic acid. The product obtained is drained, washed in water until neutralized and dried at 50° C. There are obtained 58 g (yield: 98%) of methyl 3-hydroxy-5-nitro-thianaphthene-2-carboxylate (m.p.: 215° C).

Stage D. Methyl-3-methoxy-5-nitro-thianaphthene-2-carboxylate

In a 3 liter flask equipped with an impervious agitator, a reflux refrigerant and a thermometer, there are introduced 128 g (0.50 mole) of methyl 3-hydroxy-5-nitro-thianaphthene-2-carboxylate, 900 ml of acetone, 70 g of methyl sulfate and 70 g of potassium carbonate. A suspension is obtained which is heated at 40° C. It forms a yellow mass which becomes more and more thick. After 12 hours of heating, 9 liters of water are added which dissolve the mineral salts. The methyl 3-methoxy-5-nitro-thianaphthene-2-carboxylate thus formed is drained, washed with water and dried at 40° C. There are obtained 130 g of product (yield: 96%) melting at 163° C.

Stage E.

In a flask equipped with an agitator and a thermometer, there are introduced 106 g (0.4 mole) of methyl 3-methoxy-5-nitro-thianaphthene-2-carboxylate, 630 ml of ethylene glycol and 30 g of diethylaminoethylenediamine. There is obtained a thick mass difficult to agitate. The reaction mixture is maintained at 60° C for 24 hours. The precipitate is then recovered with 2 liters of water and redissolved by the addition of acetic acid. There remains an unimportant insoluble which is filtered. The solution is then treated with 200 ml of 24% ammonia. The N-(diethylaminoethyl)-3-methoxy-5-nitro-thianaphthene-2-carboxamide is filtered washed on a filter with water and dried. It is a white solid (m.p.: 175° C).

Stage F. N-(diethylaminoethyl)-5-amino-3-methoxy-thianaphthene-2-carboxamide

The nitrited derivative obtained in stage E is placed in an autoclave under pressure with 300 ml of tetrahydrofuran and two coffee spoons of Raney nickel. Hydrogenation is carried out at a temperature of 40° C and is completed in about 1 hour.

After cooling, the solution of tetrahydrofuran is filtered to separate the Raney nickel, is concentrated on a water-bath and the product obtained is precipitated by the addition of 350 ml of water. It is in the form of pale yellow crystals (m.p.: 104° C). The hydrochloride of this corresponding base is a white solid melting at 185° C.

EXAMPLE VIII

N-(DIMETHYLAMINOETHYL)-3-METHOXY-5-AMINO-THIANAPHTHENE-2-CARBOXAMIDE

Stages A through D are the same as described in Example VII.

Stage E. 3-Methoxy-5-nitro-thianaphthene-2-carboxylic acid

In a 2 liter flask equipped with a reflux refrigerant, there are introduced 140 g (0.545 mole) of methyl 3-methoxy-5-nitro-thianaphthene-2-carboxylate, 425 ml of alcohol, 425 ml of water and 60 ml of soda lye (0.545 mole + 10% excess). The mixture is heated for 4 hours in a bain-marie. The sodium salt precipitates. The acid is precipitated by adding gently 60 ml of concentrated hydrochloric acid. The gelatinous mass obtained is agitated for several hours until a crystalized product is obtained. The 3-methoxy-5-nitro-thianaphthene-2-carboxylic acid is drained, washed with water and dried at 60° C. (yield: 98%) (m.p.: 262°–265° C).

Stage F. 3-Methoxy-5-nitro-thianaphthene-2-carbonyl chloride

In a 500 ml flask equipped with a reflux refrigerant, 174 g of thionyl chloride (4 × 0.366 mole) are introduced and then a half portion of 93g (0.366 mole) of the organic acid is added before reacting. Partial dissolution of the acid is observed at the end of 1 hour. After cooling, the reamining portion of acid is added. It is heated to 80° C. When the reaction is completed, the excess thionyl chloride is distilled under vacuum. There are obtained 98 g (99%) of 3-methoxy-5-nitro-thianaphthene-2-carbonyl chloride. (m.p.: 167°–170° C).

Stage G. N-(dimethylaminoethyl)-3-methoxy-5-nitro-thianaphthene-2-carboxamide hydrochloride In a 1 liter flask equipped with an agitator and a thermometer, there are introduced 470 ml of chloroform and 50 g of dimethylformamide. It is cooled to between +5 and +10° C and 110 g of 3-methoxy-5-nitro-thianaphthene-2-carbonyl chloride are added fractionally so as to maintain the temperature. The introduction takes about 2 hours. Agitation is continued overnight at room temperature. The following day a light insoluble is filtered and 30 ml of concentrated hydrochloric acid are added to the chloroform solution. The N-(dimethylaminoethyl)-3-methoxy-5-nitro-thianaphthene-2-carboxamide hydrochloride precipitates in the form of a yellow product which is drained and dried at 50° C (yield: 66%) (m.p.: 186° C).

Stage H. N-(dimethylaminoethyl)-3-methoxy-5-amino-thianaphthene-2-carboxamide dihydrochloride 96 G of N-(dimethylaminoethyl)-3-methoxy-5-nitro-thianaphthene- 2-carboxamide hydrochloride in 410 ml of water in the presence of 2 coffee spoons of Raney nickel are hydrogenated under pressure at a temperature of 60° C. After filtration of the nickel, the solution is made alkaline with 50 ml of 30% ammonia. The base precipitates. It is drained, washed with water and dried. There are obtained 70 g of product.

The product is redissolved in 375 ml of absolute alcohol, filtered on plant charcoal, and the solution is acidified by an alcohol solution of hydrochloric acid. The N-(dimethylaminoethyl)-3-methoxy-5-amino-thianaphthene-2-carboxamide dihydrochloride thus formed is drained, washed with alcohol and dried. There are obtained 60 g (yield: 61%) of white crystals (m.p.: 210° C).

EXAMPLE IX

RACEMIC N-(1-ETHYL--2-PYRROLIDYLMETHYL)-3-METHOXY-5-AMINO-THIANAPHTHENE-2-CARBOXAMIDE

Stages A through D are the same as described in Example VII.

Stage E. N-(1-ethyl-2-pyrrolidylmethyl)-3-methoxy-5-nitro-thianaphthene-2-carboxamide In a 2 liter flask equipped with an agitator and a thermometer, there are introduced 106 g (0.4 mole) of methyl 3-methoxy-5-nitro-thianaphthene-2-carboxylate, 640 ml of ethylene glycol and 64 g of 1-ethyl-2-aminomethyl-pyrolidine. The mixture is allowed to stand 10 days at 60° C and then the precipitate is recovered with from 2.5 to 3 liters of water and redissolved by the addition of acetic acid. The base is then precipitated by the addition of 200 ml of ammonia. There are obtained 47 g of N-(1-ethyl-2-pyrrolidylmethyl)-3-methoxy-5-nitro-thianaphthene-2-carboxamide (yield: 45.5%) (m.p.: 96° C).

Stage F. N-(1-ethyl-2-pyrrolidylmethyl)-3-methoxy-5-amino-thianaphthene-2-carboxamide 47 G of 1-ethyl-2-pyrrolidylmethyl-3-methoxy-5-nitro-thianaphthene-2-carboxamide dissolved in 140 ml of tetrahydrofuran in the presence of 2 coffee spoons of Raney nickel are hydrogenated under pressure at a temperature of 60° C. After filtration of the nickel, the tetrahydrofuran is distilled and there remain 68 g of N-(1-ethyl-2-pyrrolidylmethyl)-3-methoxy-5-amino-thianaphthene-2-carboxamide which are recovered with 100 ml of methylene chloride.

The methylene chloride is dried with sodium sulfate, then distilled under vacuum to a constant weight. The base obtained is then dissolved in warm alcohol and a solution of 14 ml of dry hydrochloric acid in 100 ml of absolute alcohol is added. The dihydrochloride of N-(1-ethyl-2-pyrrolidylmethyl)-3-methoxy-5-amino-thianaphthene-2-carboxamide formed precipitates. It is dried at low temperature, washed and dried at room temperature. White crystals are obtained (m.p.: 195° C).

EXAMPLE X

LEVO N-(1-ETHYL-2-PYRROLIDYLMETHYL)-3-METHOXY-5-AMINO-THIANAPHTHENE-2-CARBOXAMIDE

Stages A through F are the same as those described in Example VIII.

Stage G. Levo N-(1-ethyl-2-pyrrolidylmethyl)-3-methoxy-5-nitro-thianaphthene-2-carboxamide In a flask equipped with an agitator and a thermometer, there are introduced 55 g (0.427 mole) of levo 1-ethyl-2-aminomethyl-pyrrolidine and 470 ml of chloroform. A solution is obtained to which is added fractionally, 116 g (0.427 mole) of 3-methoxy-5-nitro-thianaphthene-2-carbonyl chloride in powdered form at 10°–12°C. When the introduction is completed, the temperature is allowed to rise and agitation is continued for several hours. After the addition of 200 ml of water, all of the chloroform is distilled. The hydrochloride crystalizes. There are added 250 ml of water and heating is continued to total dissolution. There remains an insoluble which is filtered with heat (9 g). The hydrochloride crystalizes on cooling. It is redissolved by heat and 43 ml of soda lye are added. The base precipitates. After cooling, it is drained, washed with water and dried at 50° C. There are obtained 143 g (yield: 92%) of levo N-(1-ethyl-2-pyrrolidylmethyl)-3-methoxy-5-nitro-thianaphthene-2-carboxamide (m.p.: 105°–106° C).

Stage H. Levo N-(1-ethyl-2-pyrrolidylmethyl)-3-methoxy-5-amino-thianaphthene-2-carboxamide 127 G (0.349 mole) of levo N-(1-ethyl-2-pyrrolidylmethyl)-3-methoxy-5-nitro-thianaphthene-2-carboxamide dissolved in 350 ml of water and 29.5 ml of concentrated hydrochloric acid in the presence of 2 coffee spoons of Raney nickel are hydrogenated under pressure at a temperature of 55° C. After filtration of the nickel, the amine base is precipitated with 60 ml of ammonia and recovered with methylene chloride. The aqueous solution is extracted in methylene chloride and the organic solution is dried with potassium carbonate. The methylene chloride is then distilled under vacuum. The base obtained is recrystalized in acetonitrile and then in dioxan. The base obtained is purified by passage through dihydrochloride and again through the free base. There are obtained 47.5 g (yield: 40%) of levo N-(1-ethyl-2-pyrrolidylmethyl)-3-methoxy-5-amino-thianaphthene-2-carboxamide (m.p.: 101°–102° C); $[\alpha]_D = -45°$ (sol. 5% dimethylformamide).

EXAMPLE XI

DEXTRO N-(1-ETHYL-2-PYRROLIDYLMETHYL)-3-METHOXY-5-AMINO-THIANAPHTHENE-2-CARBOXAMIDE

Stages A through F are the same as those described in Example VIII.

Stage G. Dextro N-(1-ethyl-2-pyrrolidylmethyl)-3-methoxy-5-amino-thianaphthene-2-carboxamide In a 1 liter flask equipped with an agitator and a thermometer, there are introduced 46 g of dextro 1-ethyl-2-aminomethylpyrrolidine and 400 ml of chloroform and the mixture is cooled to 5° C. There is added, fractionally, 3-methoxy-5-nitro-thianaphthene-2-carbonyl chloride, the temperature being maintained at between 5° and 10° C. Where the introduction is complete, the mixture is allowed to stand for one night. After the addition of 675 ml of water, the chloroform is distilled. The residue is then filtered with heat on charcoal. The hydrochloride crystalizes on cooling. It is drained, washed with water and dried at 50° C. There are obtained 135 g of product, melting at 145°–150° C.

The hydrochloride is dissolved in 600 ml of boiling water, the solution is filtered with charcoal and alkalinized with 50 ml of ammonia. The liquid base solidifies. It is drained, washed with water and dried at 50° C. There are obtained 107 g of product, melting at 105°–108° C.

Stage H. Dextro N-(1-ethyl-2-pyrrolidylmethyl)-3-methoxy-5-amino-thianaphthene-2-carboxamide 96 G (0.261 mole) of dextro N-(1-ethyl-2-pyrrolidylmethyl)-3-methoxy-5-nitro-thianaphthene-2-carboxamide in 285 ml of water and 21.6 ml of concentrated hydrochloric acid in the presence of 2 coffee spoons of Raney nickel under agitation are hydrogenated under pressure. After cooling, the nickel is filtered and the base is precipitated by the addition of ammonia. It is then drained, washed with water and dried at 40° C. The base obtained is purified by successive passage in dihydrochloride and then in the free base. There is obtained dextro N-(1-ethyl-2-pyrrolidylmethyl)-3-methoxy-5-amino-thianaphthene-2-carboxamide with a rendering of 43% (m.p.: 104°–106° C); $[\alpha]_D = +45°$ (solution 5% dimethylformamide).

The acid addition salts of the 3-alkoxy-thianaphthene-2-carboxamides of this invention may be produced by reacting the carboxamide with a mineral acid such as hydrobromic acid or an organic acid such as ethane sulfonic acid. The quaternary ammonium salts of such carboxamide may be produced by reacting the carboxamide base with an aliphatic or aromatic alkylating agent, such as methyl chloride, methyl bromide, methyl iodide, dimethyl sulfate, methyl benzene sulfonate, methyl p-toluene sulfonate, ethyl bromide, propyl bromide or benzyl chloride.

EXAMPLE XII

N-(1-ETHYL-2-PYRROLIDYLMETHYL)-3-METHOXY-5-CHLORO-THIANAPHTHENE-2-CARBOXAMIDE HYDROCHLORIDE

In a 3 liter flask equipped with an air-tight agitator, a solution of sodium methylate is prepared by dissolving 12.65 g of sodium in 700 ml of methanol. 151 g of (2-carbomethoxy-methylthio)-5-methyl chlorobenzoate are added fractionally. The mixture is allowed to react without heating for one day and then 65 ml of acetic acid are added which precipitates the 3-hydroxy-5-chlorothianaphthene-2-methyl carboxylate. It has a melting point of 158°C. The precipitate is washed and dried. It is placed in suspension in 625 ml of acetone with 71 g of methyl sulfate. It is heated to 40°C and 71 g of potassium carbonate are added. It is refluxed for 3 hours. 500 ml of acetone are distilled and the residue is recovered in 2 liters of water. The 3-methoxy-5-chloro-thianaphthene-2-methyl carboxylate precipitates. It is recovered and then dissolved in 500 ml of alcohol at 95°C. 51 ml of 30% soda are added and reflux is maintained for 1 hour. Water is added to dissolve the sodium salt formed and the insoluble traces are filtered. The 3-methoxy-5-chloro-thianaphthene-2-carboxylic acid is precipitated with 50 ml of concentrated hydrochloric acid. The 145 g of acid obtained (0.6 mole) are introduced, in two portions, into a flask containing 357 g of thionyl chloride. It is heated to 60°C to aid dissolution and then the second portion is added. It is refluxed to obtain the 3-methoxy-5-chloro-thianaphthene-2-carbonyl chloride which is washed with petroleum ether and dried.

Into a 1 liter flask, 36.5 g of 1-ethyl-2-aminomethyl pyrrolidine dissolved in 400 ml of methylethylketone are introduced. 74 g of acid chloride obtained above are added and heated to 30°C. When the introduction is completed, a precipitate appears which crystallizes in 30 minutes. It is filtered, washed with methylethylketone and dried at 55°C. 95 g of N-(1-ethyl-2-pyrrolidylmethyl)-3-methoxy-5-chloro-thianaphthene-2-carboxamide hydrochloride are obtained, having a melting point of 140°C. (Yield: 86%)

EXAMPLE XIII

N-(MORPHOLINOPROPYL)-3-ETHOXY-5-BROMOTHIANAPHTHENE-2-CARBOXAMIDE-PHOSPHATE

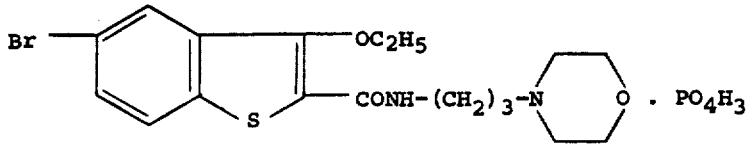

Into a 250 ml flask, equipped with an air-tight agitator, an ascending refrigerant and a thermometer, there are introduced 30 g of 3-ethoxy-5-bromothianaphthene-2-carboxylic acid. 36 ml of thionyl chloride are added and the mixture is heated at 70°C for 2 hours. The excess of thionyl chloride is then removed to obtain 32 g of acid chloride melting at 117°–118°C.

In a 500 ml flask, 14.4 g of morpholinopropylamine are dissolved in 110 ml of methylethylketone. The acid chloride is added under agitation and cooled at 0°C, avoiding going below 5°C. When the addition is complete, the temperature is allowed to go to 22°C. The crystals of hydrochloride formed are dried and washed with 30 ml of methylethylketone. They are dissolved in 200 ml of water and the carboxamide is precipitated with 50 ml of ammonia. It is extracted with sulfuric ether and the etherized extracts washed in water. The ether is evaporated to obtain 26 g of N-morpholinopropyl-3-ethoxy-5-bromothianaphthene-2-carboxamide.

The carboxamide is dissolved in 26 ml of absolute alcohol and 7 g of orthophosphoric acid dissolved in 10 ml of absolute alcohol are added. The mixture is cooled and agitated. The phosphate crystallizes. It is separated, washed in alcohol and dried. Its melting point is 178°C.

EXAMPLE XIV

N-(MORPHOLINOETHYL)-3-METHOXY-5-NITRO-THIANAPHTHENE-2-CARBOXAMIDE

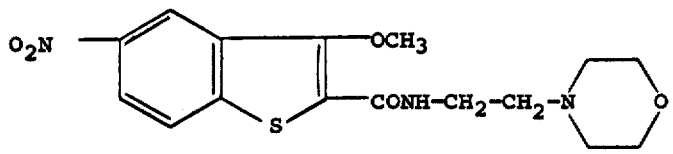

Into a 1 liter flask, equipped with a mechanical agitator and a thermometer, are introduced 45 g of morpholinoethylamine dissolved in 384 ml of chloroform. It is cooled to 3°C and 90 g of 3-methoxy-5-nitrothianaphthene-2-carboxyl chloride by fractions are introduced, the temperature being maintained between 5° and 10°C.

When the introduction is completed, it is left under agitation at room temperature for 4 to 5 hours. It is allowed to stand for one night. The N-(morpholinoethyl)-3-methoxy-5-nitrothianaphthene-2-carboxamide crystallizes. It is dried, washed with a little acetone and dried again. 107 g of crystals are obtained, having a melting point of 250°C. (Yield: 80%)

EXAMPLE XV

N-(PYRROLIDINOETHYL)-3-ETHOXY-5-BROMOTHIANAPHTHENE-2-CARBOXAMIDE HYDROCHLORIDE

Into a 500 ml flask, equipped with a mechanical agitator, a thermometer and a dropping funnel, there are introduced 12 g of pyrrolidinoethylamine dissolved in 150 ml of methylethylketone. It is cooled at 0°C and 32 g of 3-ethoxy-5-bromo-thianaphthene-2-carboxyl chloride are introduced fractionally, the temperature being maintained below 10°C.

When the addition is complete, the mixture is agitated for one hour. The methylethylketone is distilled under vacuum and the residue is recovered with ammonia to precipitate the base. It is extracted with chloroform, and after being washed in water, it is dried with anhydrous potassium carbonate. The chloroform is distilled to obtain the free base in the form of a red liquid.

The free base obtained [N-(pyrrolidinoethyl)-3-ethoxy-5-bromo-thianaphthene-2-carboxamide] is dissolved in absolute ethanol and the hydrochloride is obtained by the addition of dry hydrochloric acid in ethanol. The precipitate obtained is recrystallized twice to give 20 g of hydrochloride melting at 166°C. (Yield: 46%)

EXAMPLE XVI

N-(PYRROLIDINOETHYL)-3-ETHOXY-5-NITRO-THIANAPHTHENE-2-CARBOXAMIDE HYDROCHLORIDE

In a 2 liter flask equipped with a mechanical agitator, there are dissolved 100 g of 3-hydroxy-5-nitro-thianaphthene-2-methyl carboxylate in 700 ml of methylethylketone and 79 g of anhydrous potassium carbonate are added. It is refluxed and 50 ml of dimethyl sulfate are added. It is refluxed for 8 hours and is diluted with water to precipitate 3-ethoxy-5-nitro-thianaphthene-2-methyl carboxylate. It is washed in water and dried at 50°C.

In a 500 ml flask, 50 g of 3-ethoxy-5-nitro-thianaphthene-2-methyl carboxylate obtained as above, are agitated with 135 ml of ethanol, 110 ml of water and 30 ml of sodium hydroxide at 36° Be. It is refluxed for 2 hours, then poured into 300 ml of water and 3-ethoxy-5-nitro-thianaphthene-2-carboxylic acid is precipitated with 40 ml of hydrochloric acid, is washed and dried. The chloride of this acid is made by the addition of 100 ml of thionyl chloride to 39 g of acid.

20 g of pyrrolidinoethylamine are dissolved in 100 ml of chloroform and this solution is cooled at 0°C. The acid chloride prepared above is introduced, the temperature being maintained between 0° and 5°C. The precipitate is then agitated for 3 hours before drying and washing it with a few milliliters of chloroform.

50 g of N-(pyrrolidinoetyl)-3-ethoxy-5-nitro-thianaphthene-2-carboxamide hydrochloride are obtained, having a melting point of 210°C.

EXAMPLE XVII

N-(PYRROLIDINOETHYL)-3-ETHOXY-5-AMINO-THIANAPHTHENE-2-CARBOXAMIDE HYDROCHLORIDE

In a 1 liter autoclave, 50 g of hydrochloride obtained as above are combined with 300 ml of water and 3 coffee spoonfuls of Raney nickel. Hydrogen is passed through to attain 120 kg of pressure, at 30°C. It is then heated at 70°C and agitated for 3 hours before cooling. The hydrogenation is then stopped, the nickel separated and the product sought precipitated with 50 ml of ammonia. The product is washed and dried. It has a melting point of 126°C.

EXAMPLE XVIII

N-DIETHYLAMINOETHYL-3-METHOXY-THIANAPHTHENE-2-CARBOXAMIDE-METHYL-BROMIDE

To 1.3 g of N-(diethylaminoethyl)-3-methoxy-thianaphthene-2-carboxamide in 15 ml of acetone is added 4 ml of a solution of 0.25 mg of methylbromide per liter of acetone. The mixture is permitted to stand for a period of about 17 hours, such as overnight. The precipitate formed is filtered and dried in an oven.

The mixture so obtained still contains about 50% of the free base. For purification, the mixture is poured into water in which is partially dissolves. After filtration and evaporation of the aqueous solution, the N-(diethylaminoethyl)-3-methoxy-thianaphthene-2-carboxamide-methylbromide, having an m.p. of 155°–160°C, is obtained.

Methylbromides of other 3-alkoxy-thianaphthene-2-carboxamides are obtained by substituted 1.3 g of the required base dissolved in 15 ml of acetone instead of 1.3 g of N-(diethylaminoethyl)-3-methoxy-thianaphthene-2-carboxamide employed in this Example and otherwise following the procedure described in this Example.

In like manner, the methylbromides of the following thianaphthenes may be obtained:

N-(diethylaminoethyl)-3-methoxy-5-chloro-thianaphthene-2-carboxamide (m.p.: 157°–160°C)

N-(diethylaminoethyl)-3,5-dimethoxy-thianaphthene-2-carboxamide (m.p.: 136°–139°C)

N-(diethylaminoethyl)-3,5,7-trimethoxy-thianaphthene-2-carboxamide (m.p.: 184°–188°C)

N-(diethylaminoethyl)-3-methoxy-5-bromo-thianaphthene-2-carboxamide (m.p.: 181°–182°C)

EXAMPLE XIX

N-(MORPHOLINOPROPYL)-3-ETHOXY-5-BROMO-THIANAPHTHENE-2-CARBOXAMIDE METHYLBROMIDE

To 1.3 g of N-(morpholinopropyl)-3-ethoxy-5-bromo-thianaphthene-2-carboxamide in 15 ml of acetone is added 4 ml of a solution of 0.25 mg of methylenebromide per liter of acetone. The mixture is permitted to stand for a period of approximately 17 hours. The precipitate formed is filtered and dried in an oven. The mixture so obtained contains about 50% of the free base. For purification, the mixture is poured into water in which it partially dissolves. After filtration and evaporation of the aqueous solution, the N-(morpholinopropyl)-3-ethoxy-5-bromo-thianaphthene-2-carboxamide methylbromide is obtained.

Methylbromide of other 3-alkoxy-thianaphthene-2-carboxamides are obtained by substituting 1.3 g of the required base dissolved in 15 ml of acetone instead of 1.3 g of N-(morpholinopropyl)-3-ethoxy-5-bromo-thianaphthene-2-carboxamide employed in this Example and otherwise following the procedure described in this Example.

Examples of methylbromides of other 3-alkoxy-thianaphthene-2-carboxamides which may be obtained by practice of the procedures of this Examples are:

N-(morpholinoethyl)-3-methoxy-5-nitro-thianaphthene-2-carboxamide methylbromide

N-(pyrrolidinoethyl)-3-ethoxy-5-bromo-thianaphthene-2-carboxamide methylbromide

N-(pyrrolidinoethyl)-3-ethoxy-5-nitro-thianaphthene-2-carboxamide methylbromide

N-(pyrrolidinoethyl)-3-ethoxy-5-amino-thianaphthene-2-carboxamide methylbromide

Compositions of this invention have been pharmacologically studied to determine their lack of toxicity on the one hand and their anti-emetic activity and central nervous system activity on the other hand.

The low toxicities which were studied in the mouse showed that the compositions of this invention have a toxicity entirely compatible with therapeutic use. The results are given in the following table:

| COMPOSITIONS | I.V. | DL$_{50}$ Base mg/kg I.P. | S.C. | P.O. |
|---|---|---|---|---|
| N-(diethylaminoethyl)-3-methoxy-thianaphthene-2-carboxamide | 25.8–29.5 | 105–114 | 164–168 | 273–286 |
| N-(diethylaminoethyl)-3-methoxy-5-amino-thianaphthene-2-carboxamide | 49.9–52.6 | 109–112 | 125 | 242–273 |
| N-(diethylaminoethyl)-3-5-6-trimethoxy-thianaphthene-2-carboxamide | 36.4–37 | — | 54–61.5 | — |
| N-(1-ethyl-2-pyrrolidylmethyl)-3-methoxy-thianaphthene-2-carboxamide | 18.9–19.3 | 124–134 | 159 | 306–333 |
| N-(1-ethyl-2-pyrrolidylmethyl)-3-methoxy-5-aminothianaphthene-2-carboxamide | 31.4–33.4 | 91.9–92.3 | 86.4–94.2 | — |
| N-(1-ethyl-2-pyrrolidylmethyl)-3-5-6-trimethoxy | | | | |

-continued

| COMPOSITIONS | DL$_{50}$ Base mg/kg | | | |
|---|---|---|---|---|
| | I.V. | I.P. | S.C. | P.O. |
| thianaphthene-2-carboxamide | 36–36.9 | 70–76 | 60–65 | — |
| N-(diethylaminoethyl)-1-1-dioxy-3-methoxy-thianaphthene-2-carboxamide | 88 | 257–260 | 447–451 | 1106 |
| N-(1-ethyl-2-pyrrolidylmethyl)-1-1-dioxy-3-methoxy-thianaphthene-2-carboxamide | 45.3 | 149–159 | 253–281 | — |

The antiemetic action of these compositions on the vomiting centers was studied in the dog with the aid of apomorphine following the technique of CHEN and ENSOR together with DUCROT and P. DECOURT. Lots of 4 dogs were worked with.

The apomorphine was administered subcutaneously in dosage of 0.10 mg/kg. The compositions studied were administered 30 minutes before, also subcutaneously. The vomitings were counted during the 30 minutes following the injection of the apomorphine.

The following numbers were arrived at from the experimental results for many of the compositions of the present invention.

| COMPOSITIONS | Rate of Protection in Dosages of 250 μg/kg Base |
|---|---|
| N-(diethylaminoethyl)-3-methoxy-thianaphthene-2-carboxamide | 100% |
| N-(dimethylaminoethyl)-3-methoxy-5-amino-thianaphthene-2-carboxamide | 100% |
| N-(diethylaminoethyl)-3-methoxy-5-amino-thianaphthene-2-carboxamide | 100% |
| N-(diethylaminoethyl)-3-5-6-trimethoxy-thianaphthene-2-carboxamide | 100% |
| N-(1-ethyl-2-pyrrolidylmethyl)-3-methoxy-thianaphthene-2-carboxamide | 100% |
| N-(1-ethyl-2-pyrrolidylmethyl)-3-methoxy-5-amino-thianaphthene-2-carboxamide (Racemic mixture of levo and dextro forms) | 100% |
| N-(1-ethyl-2-pyrrolidylmethyl)-3-methoxy-5-amino-thianaphthene-2-carboxamide (levo form) | 100% |
| N-(1-ethyl-2-pyrrolidylmethyl)-3-methoxy-5-amino-thianaphthene-2-carboxamide (dextro form) | 100% |
| N-1-ethyl-2-pyrrolidylmethyl)-3-5-6-trimethoxy-thianaphthene-2-carboxamide | 100% |
| N-(diethylaminoethyl)-1-dioxy-3-methoxy-thianaphthene-2-carboxamide | 100% |
| N-(1-ethyl-2-pyrrolidylmethyl)-1-dioxy-3-methoxy-thianaphthene-2-carboxamide | 100% |

Other pharmacological properties of these compositions were proved by means of various tests which showed their excellent modifying action on the central nervous system. These tests are summarized in the following tables for many of the compositions of this invention.

| CATALEPTIC ACTIVITY IN THE MOUSE COMPOSITIONS | DE$_{50}$ Base mg/kg/S.C. |
|---|---|
| N-(diethylaminoethyl)-3-methoxy-thianaphthene-2-carboxamide | 15.9 (7 h) |
| N-(diethylaminoethyl)-3-methoxy-5-amino-thianaphthene-2-carboxamide | — |
| N-(diethylaminoethyl)-3-5-6-trimethoxy-thianaphthene-2-carboxamide | — |
| N-(1-ethyl-2-pyrrolidylmethyl)-3-methoxy-thianaphthene-2-carboxamide | 2–2.2 (6 h) |
| N-(1-ethyl-2-pyrrolidylmethyl)-3-methoxy-5-amino-thianaphthene-2-carboxamide | 17.3 (7 h) |
| N-(1-ethyl-2-pyrrolidylmethyl)-3-5-6-trimethoxy-thianaphthene-2-carboxamide | 8 (7 h) |
| N-(diethylaminoethyl)-1-dioxy-3-methoxy-thianaphthene-2-carboxamide | — |
| N-(1-ethyl-2-pyrrolidylmethyl)-1-1-dioxy-3-methoxy-thianaphthene-2-carboxamide | 13.6 (7 h) |

| ACTION ON MOTILITY OF THE MOUSE (TEST OF WINTER AND FLATAKER) COMPOSITIONS | DE$_{50}$ Base mg/kg/I.P. |
|---|---|
| N-(diethylaminoethyl)-3-methoxy-thianaphthene-2-carboxamide | 14.1 |
| N-(diethylamino)-3-methoxy-5-amino-thianaphthene-2-carboxamide | 8.6 |
| N-(diethylaminoethyl)-3-5-6-trimethoxy-thianaphthene-2-carboxamide | — |
| N-(1-ethyl-2-pyrrolidylmethyl)-3-methoxy-thianaphthene-2-carboxamide | 1.9–2.5 |
| N-(1-ethyl-2-pyrrolidylmethyl)-3-methoxy-5- | |

| ACTION ON MOTILITY OF THE MOUSE (TEST OF WINTER AND FLATAKER) COMPOSITIONS | $DE_{50\ Rose}$ mg/kg/I.P. |
|---|---|
| amino-thianaphthene-2-carboxamide | 2.9–3.1 |
| N-(1-ethyl-2-pyrrolidylmethyl)-3-5-6-trimethoxy-thianaphthene-2-carboxamide | 31–34 |
| N-(diethylaminoethyl)-1-1-dioxy-3-methoxy-thianaphthene-2-carboxamide | 97.5 |
| N-(1-ethyl-2-pyrrolidylmethyl)-1-1-dioxy-3-methoxy-thianaphthene-2-carboxamide | 76.1–78.8 |

| ACTION ON THE MOTILITY OF THE MOUSE (ACTION GRAPH OF KRAUTHAMER) COMPOSITIONS | $DE_{50\ Rose}$ mg/kg I.P. |
|---|---|
| N-(diethylaminoethyl)-3-methoxy-thianaphthene-2-carboxamide | 6.4–6.8 |
| N-(diethylaminoethyl)-3-methoxy-5-amino-thianaphthene-2-carboxamide | — |
| N-(diethylaminoethyl)-3-5-6-trimethoxy-thianaphthene-2-carboxamide | 17.8 |
| N-(1-ethyl-2-pyrrolidylmethyl)-3-methoxy-thianaphthene-2-carboxamide | 1.3 |
| N-(1-ethyl-2-pyrrolidylmethyl)-3-methoxy-5-amino-thianaphthene-2-carboxamide | — |
| N-(1-ethyl-2-pyrrolidylmethyl)-3-5-6-trimethoxy-thianaphthene-2-carboxamide | 18 |
| N-(diethylaminoethyl)-1-1-dioxy-3-methoxy-thianaphthene-2-carboxamide | — |
| N-(1-ethyl-2-pyrrolidylmethyl)-1-1-dioxy-3-methoxy-thianaphthene-2-carboxamide | 63.4 65.2 |

| TEST OF BODY TURNING IN THE MOUSE | | |
|---|---|---|
| COMPOSITIONS | $DE_{50\ Rose}$ mg/kg/I.P. | OBSERVATIONS |
| N-(diethylaminoethyl)-3-methoxy-thianaphthene-2-carboxamide | 28 (10 mn) | |
| N-(diethylaminoethyl)-3-methoxy-5-amino-thianaphthene 2-carboxamide | 31.2 (10 mn) | |
| N-(diethylaminoethyl)3-5-6-trimethoxy-thianaphthene-2-carboxamide | | 20 mg/kg : effect of 5% |
| N-(1-ethyl-2-pyrrolidylmethyl) 3-methoxy-thianaphthene-2-carboxamide | 13–16.8 (10 mn) | |
| N-(1-ethyl-2-pyrrolidylmethyl) 3-methoxy-5-amino-thianaphthene-2-carboxamide | 25.1–23.2 | |
| N-(1-ethyl-2-pyrrolidylmethyl) 3-5-6-trimethoxy-thianaphthene-2-carboxamide | 39.5 (10 mn) | |
| N-(diethylaminoethyl)-1-1-dioxy-3-methoxy-thianaphthene-2-carboxamide | | 100 mg/kg : effect of 17% |
| N-(1-ethyl-2-pyrrolidylmethyl)-1-1-dioxy-3-methoxy-thianaphthene-2-carboxamide | | 60 mg/kg : effect of 0% |

| TEST OF TRACTION IN THE MOUSE (COURVOISIER - JULOU) | | |
|---|---|---|
| COMPOSITIONS | $DE_{50\ Rose}$ mg/kg S.C. | OBSERVATIONS |
| N-(diethylaminoethyl)-3-methoxy-thianaphthene-2-carboxamide | 40.9 | |
| N-(diethylaminoethyl)-3-methoxy-5-amino-thianaphthene-2-carboxamide | | 100 mg/kg : effect of 20% |
| N-(diethylamino)-3-5-6-trimethoxy-thianaphthene-2-carboxamide | | 30 mg/kg : effect of 30% |
| N-(1-ethyl-2-pyrrolidylmethyl)-3-methoxy-thianaphthene-2-carboxamide | 46 | |
| N-(1-ethyl-2-pyrrolidylmethyl)-3-methoxy-5-aminothianaphthene-2-carboxamide | | 40 mg/kg : effect of 0% |
| N-(1-ethyl-2-pyrrolidylmethyl)-3-5-6-trimethoxy-thianaphthene-2-carboxamide | | 40 mg/kg : effect of 33% |
| N-(diethylaminoethyl)-1-1-dioxy-3-methoxy-thianaphthene-2-carboxamide | | 200 mg/kg : effect of 10% |
| N-(1-ethyl-2-pyrrolidylmethyl)-1-1-dioxy-3-methoxy-thianaphthene-2- | | |

-continued

TEST OF TRACTION IN THE MOUSE
(COURVOISIER - JULOU)

| COMPOSITIONS | DE$_{50}$ $_{Raw}$ mg/kg S.C. | OBSERVATIONS |
|---|---|---|
| carboxamide | | 80 mg/kg : effect of 0% |

INFLUENCE ON THE BARBITURIC NARCOSIS IN THE MOUSE

| COMPOSITIONS | DE$_{50}$ $_{Raw}$* mg/kg/I.P. | OBSERVATIONS |
|---|---|---|
| N-(diethylaminoethyl)-3-methoxy-thianaphthene-2-carboxamide | | 40 mg/kg : index = 1.18 |
| N-(diethylaminoethyl)-3-methoxy-5-amino-thianaphthene-2-carboxamide | 31.2 (30 mn) | |
| N-(diethylaminoethyl)-3-5-6-trimethoxy-thianaphthene-2-carboxamide | | 20 mg/kg : index = 1.46 |
| N-(1-ethyl-2-pyrrolidyl-methyl)-3-methoxy-thianaphthene-2-carboxamide | | 40 mg/kg : index = 0.76 |
| N-(1-ethyl-2-pyrrolidyl-methyl)-3-methoxy-5-amino-thianaphthene-2-carboxamide | 78-86.4 | |
| N-(1-ethyl-2-pyrrolidyl-methyl)-3-5-6-trimethoxy-thianaphthene-2-carboxamide | | 40 mg/kg : index = 1.06 |
| N-(diethylaminoethyl)-1-1-dioxy-3-methoxy-thianaphthene-2-carboxamide | 181 (30 mn) | |
| N-(ethyl-2-pyrrolidyl-methyl)-1-1-dioxy-3-methoxy-thianaphthene-2-carboxamide | | 100 mg/kg : index = 1.81 |

*Dose corresponding to index 2 (doubling of time of hypnosis).

TEST WITH APOMORPHINE IN THE RAT
(JANSSEN)

| COMPOSITIONS | DE$_{50}$ $_{Raw}$ mg/kg/S.C. | OBSERVATIONS |
|---|---|---|
| N-(diethylaminoethyl)-3-methoxy-thianaphthene-2-carboxamide | 30.3-35.6 | |
| N-(diethylaminoethyl)-3-methoxy-5-amino-thianaphthene-2-carboxamide | 76.4-77.9 | |
| N-(diethylaminoethyl)-3-5-6-trimethoxy-thianaphthene-2-carboxamide | 72 | |
| N-(1-ethyl-2-pyrrolidylmethyl)-3-methoxy-thianaphthene-2-carboxamide | 4.05-4.7 | |
| N-(1-ethyl-2-pyrrolidylmethyl)-3-methoxy-5-aminothianaphthene-2-carboxamide | 6-7.1 | |
| N-(1-ethyl-2-pyrrolidylmethyl)-3-5-6-trimethoxy-thianaphthene-2-carboxamide | 26.5-30 | |
| N-(diethylaminoethyl)-1-1-dioxy-3-methoxy-thianaphthene-2-carboxamide | | 200 mg/kg : effect of 0% |
| N-(1-ethyl-2-pyrrolidylmethyl)-1-1-dioxy-3-methoxy-thianaphthene-2-carboxamide | | 200 mg/kg : effect of 0% |

| COMPOSITIONS | DE$_{50}$ $_{Raw}$ mg/kg/P.O. | TEST WITH MORPHINE IN THE MOUSE OBSERVATIONS |
|---|---|---|
| N-(diethylaminoethyl)-3-methoxy-thianaphthene-2-carboxamide | — | |
| N-(diethylaminoethyl)-3-methoxy-5-amino-thianaphthene-2-carboxamide | — | |
| N-(diethylaminoethyl)-3-5-6-trimethoxy-thianaphthene-2-carboxamide | — | |

TEST WITH MORPHINE IN THE MOUSE -continued

| COMPOSITIONS | DE$_{50}$ mg/kg/P.O. | OBSERVATIONS |
|---|---|---|
| N-(1-ethyl-2-pyrrolidylmethyl)-3-methoxy-thianaphthene-2-carboxamide | 42 | |
| N-(1-ethyl-2-pyrrolidylmethyl)-3-methoxy-5-amino-thianaphthene-2-carboxamide | 62.8 | |
| N-(1-ethyl-2-pyrrolidylmethyl)-3-5-6-trimethoxy-thianaphthene-2-carboxamide | — | |
| N-(diethylaminoethyl)-1-1-dioxy-3-methoxy-thianaphthene-2-carboxamide | — | |
| N-(1-ethyl-2-pyrrolidylmethyl)-1-1-dioxy-3-methoxy-thianaphthene-2-carboxamide | | 400 mg/kg : effect of 38% |

TEST WITH TREMORINE IN THE MOUSE

| COMPOSITIONS | DE$_{50}$ mg/kg/I.P. | OBSERVATIONS |
|---|---|---|
| N-(diethylaminoethyl)-3-methoxy-thianaphthene-2-carboxamide | | 400 mg/kg : effect of 5% |
| N-(diethylaminoethyl)-3-methoxy-5-amino-thianaphthene-2-carboxamide | | 80 mg/kg : effect of 28% |
| N-(diethylaminoethyl)-3-5-6-trimethoxy-thianaphthene-2-carboxamide | — | |
| N-(1-ethyl-2-pyrrolidylmethyl)-3-methoxy-thianaphthene-2-carboxamide | | 40 mg/kg : effect of 10% |
| N-(1-ethyl-2-pyrrolidylmethyl)-3-methoxy-5-amino-thianaphthene-2-carboxamide | | 60 mg/kg : effect of 11% |
| N-(1-ethyl-2-pyrrolidylmethyl-3-5-6-trimethoxy-thianaphthene-2-carboxamide | | 30 mg/kg : effect of 21% |
| N-(diethylaminoethyl)-1-1-dioxy-3-methoxy-thianaphthene-2-carboxamide | | 100 mg/kg : effect of 16% |
| N-(1-ethyl-2-pyrrolidylmethyl)-1-1-dioxy-3-methoxy-thianaphthene-2-carboxamide | | 80 mg/kg : effect of 5% |

The experimental results have been confirmed in the clinic where the products were administered in the form of tablets or ampoules of a pharmaceutically acceptable salt.

Treatments were made under clinical conditions in accordance with pharmacodynamics, with no manifestation of medicament intolerance.

The compositions of this invention can be administered in the form of a pharmaceutically acceptable salt in pills, injectable or aerosol ampoules, suppositories, granulated sweetener and sweetened syrup.

These medicaments may be administered in the form of ampules, tablets, drops or in drinkable solutions containing pharmaceutically acceptable salts of a compound of this invention. The compounds of this invention with or without other compatible therapeutic ingredients, fillers or adjuvents may be conveniently administered in dosage unit forms. For example, the following formulation may be used for compressed tablet dosage form:

| | |
|---|---|
| active ingredient | 60 mg |
| spray dried lactose | 266 mg |
| starch | 20 mg |
| magnesium stearate | 4 mg |

The spray dried lactose, magnesium stearate, starch and active ingredient may be mixed uniformly and then compressed directly into tablets.

For use in capsule dosage form, the active ingredient may be mixed with a suitable quantity of lactose until uniform and the capsules may be filled either by hand or by suitable mechanical means. A capsule formulation is as follows:

| | |
|---|---|
| active ingredient | 75 mg |
| lactose q. s. to 300 | |

The daily dosage may vary over wide limits for the treatment of emesis or behavior disturbances as determined by the veterinarian or physician. Desirably, the daily dosage may range from 50 to 500 µg/kg.

What is claimed is:

1. A compound selected from the group consisting of 3-alkoxy-thianaphthene-2-carboxamides and the dioxides thereof and the pharmaceutically acceptable acid addition salts of said carboxamides, said 3-alkoxy-thianaphthene-2-carboxamides having the formula:

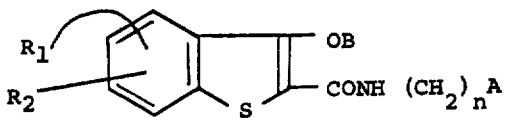

in which $R_1$ and $R_2$ are the same or different and are hydrogen, alkoxy of less than 5 carbon atoms, halogen, nitro or amino; B is alkyl of less than 5 carbon atoms or allyl; n is 1, 2 or 3; and A is selected from the class consisting of piperidinyl, imidazolidinyl, piperazino, pyrrolidino and morpholino.

2. A compound of claim 1, said compound being N-(morpholinopropyl)-3-ethoxy-5-bromo-thianaphthene-2-carboxamide phosphate.

3. A compound of claim 1, said compound being N-(morpholinoethyl)-3-methoxy-5-nitro-thianaphthene-2carboxamide.

4. A compound of claim 1, said compound being N-(pyrrolidinoethyl)-3-ethoxy-5-bromo-thianaphthene-2-carboxamide hydrochloride.

5. A compound of claim 1, said compound being N-pyrrolidinoethyl)-3-ethoxy-5-nitro-thianaphthene-2carboxamide hydrochloride.

6. A compound of claim 1, said compound being N-(pyrrolidinoethyl)-3-ethoxy-5-amino-thianaphthene-2-carboxamide hydrochloride.

7. A quaternary ammonium salt of an N-(dialkylaminoethyl)-3-alkoxy-thianaphthene-2-carboxamide selected from the group consisting of the methylbromides of N-(diethylaminoethyl)-3-methoxy-thianaphthene-2-carboxamide, N-(diethylaminoethyl)-3-methoxy-5-chlorothianaphthene-2-carboxamide, N-(diethylaminoethyl)-3,5-dimethoxy-thianaphthene-2-carboxamide, N-(diethylaminoethyl)-3,5,7-trimethoxythianaphthene-2-carboxamide, N-(diethylaminoethyl)-3-methoxy-5-bromo-thianaphthene-2-carboxamide, N-(morpholinoproyl)-3-ethoxy-5-bromo-thianaphthene-2-carboxamide, N-(morpholinoethyl)-3-methoxy-5-nitro-thianaphthene-2-carboxamide, N-(pyrrolidinoethyl)-3-ethoxy-5-bromo-thianaphthene-2-carboxamide, N-(pyrrolidinoethyl)-3-ethoxy-5-nitro-thianaphthene-2-carboxamide and N-(pyrrolidinoethyl)-3-ethoxy-5-amino-thianaphthene-2-carboxamide.

8. A quaternary ammonium salt of claim 7, said salt being N-(diethylaminoethyl)-3-methoxy-thianaphthene-2-carboxamide methylbromide.

9. A quaternary ammonium salt of claim 7, said salt being N-(diethylaminoethyl)-3-methoxy-5-chlorothianaphthene-2-carboxamide methylbromide.

10. A quaternary ammonium salt of claim 7, said salt being N-(dimethylaminoethyl)-3,5-dimethoxythianaphthene-2-carboxamide methylbromide.

11. A quaternary ammonium salt of claim 7, said salt being N-(diethylaminoethyl)-3,5,7-trimethoxythianaphthene-2-carboxamide methylbromide.

12. A quaternary ammonium salt of claim 7, said salt being N-(diethylaminoethyl)-3-methoxy-5-bromothianaphthene-2-carboxamide methylbromide.

* * * * *